Figure 1:
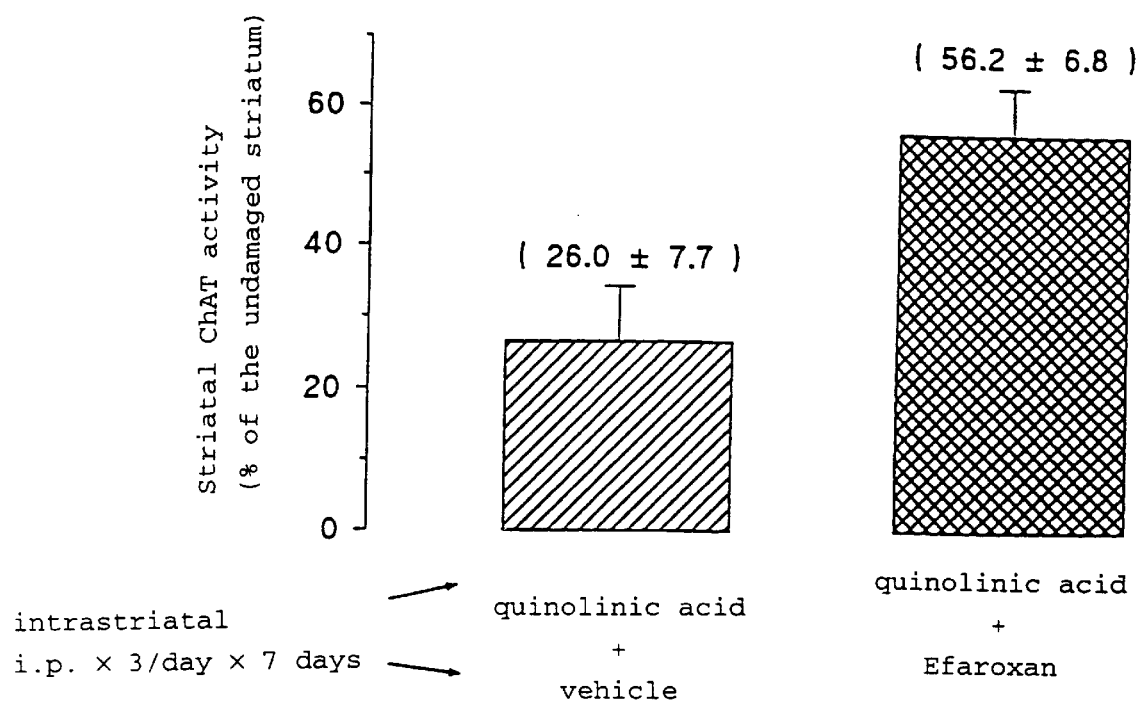

United States Patent [19]
Marien et al.

[11] Patent Number: 6,153,638
[45] Date of Patent: Nov. 28, 2000

[54] USE OF EFAROXAN FOR PRODUCING MEDICINE FOR TREATING HUNTINGTON'S DISEASE

[75] Inventors: Marc Marien; Jean-Claude Martel; Francis Colpaert, all of Castres; Thierry Imbert, Viviers-les-Montagnes, all of France

[73] Assignee: Pierre Fabre Medicament, Boulogne-Billancourt, France

[21] Appl. No.: 09/242,314

[22] PCT Filed: Aug. 12, 1997

[86] PCT No.: PCT/FR97/01480

§ 371 Date: Feb. 12, 1999

§ 102(e) Date: Feb. 12, 1999

[87] PCT Pub. No.: WO98/06393

PCT Pub. Date: Feb. 19, 1998

[30] Foreign Application Priority Data

Aug. 12, 1996 [FR] France .................................. 96 10118

[51] Int. Cl.[7] .................................................. A61K 31/415
[52] U.S. Cl. ........................... 514/402; 514/401; 514/397
[58] Field of Search ............................. 514/378, 12, 397, 514/250, 401, 402; 530/350; 544/344, 345

[56] References Cited

U.S. PATENT DOCUMENTS

| | | | |
|---|---|---|---|
| 4,889,855 | 12/1989 | Jacobsen et al. | 514/250 |
| 4,912,108 | 3/1990 | Jacobsen et al. | 514/250 |
| 5,273,989 | 12/1993 | Schwab et al. | 514/378 |
| 5,739,284 | 4/1998 | Hediger et al. | 530/350 |
| 5,741,778 | 4/1998 | Martin et al. | 514/12 |

FOREIGN PATENT DOCUMENTS

WO9501791A 7/1994 WIPO.

OTHER PUBLICATIONS

G. Olmos et al, "Imidazoli(di)ne Compounds Interact with the Phencyclidine Site of NMDA Receptors in the rat brain", Eur J. Pharmacol, vol. 310, No. 2/3 (1996) pp. 273–276.

H.C. Jackson et al, "Exploring the Pharmacology of the Pro–Convulsant Effects of Alpha–2–Adrenoceptor Antagonists in Mice", Psychopharmacology, vol. 105, No. 4 (1991) pp. 558–562.

*Primary Examiner*—William R. A. Jarvis
*Assistant Examiner*—Vickie Kim
*Attorney, Agent, or Firm*—The firm of Gordon W. Hueschen

[57] ABSTRACT

The invention concerns the use of efaroxan or therapeutically-acceptable salts, in its racemic form or in the form of an optically-active isomer, for treating Huntington's disease.

6 Claims, 2 Drawing Sheets

USE OF EFAROXAN FOR PRODUCING MEDICINE FOR TREATING HUNTINGTON'S DISEASE

The present application is a U.S. National Application filed under 35 USC 371 of PCT/FR97/01480, filed Aug. 12, 1997 based upon French application Serial No. 96/10118 filed Aug. 12, 1996.

The present invention relates to the use of Efaroxan, which is the compound of the following formula:

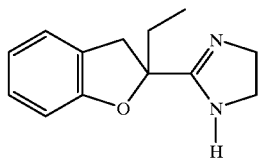

as well as its therapeutically acceptable salts, its racemic form or its optically active isomers, for the preparation of a medicinal product for the treatment of Huntington's disease.

The subject of the present invention is the use of Efaroxan to obtain a neuroprotective medicinal product for the treatment of Huntington's disease and its progression.

Huntington's disease is considered as a pathological consequence of lesions of the GABA-ergic and cholinergic systems in the striatum which are caused by excitotoxic substances on the complex: ion channels-NMDA receptor.

The clinical manifestations of Huntington's disease are motor disorders, in particular abnormal choreiform movements which gradually worsen and are subsequently accompanied by bradykinesia and muscular rigidity, as well as by neuropsychiatric problems such as depression, suicidal tendencies and personality and cognitive disorders. These disorders are very soon manifested by a loss of visuospatial acuity which can precede the choreiform movements by a few years, with cognitive loss as is observed in patients whose frontal lobe is affected.

One particular aspect of the disease is memory loss, in particular the recall function. In neuropathological terms, one characteristic of the disease is a marked atrophy of the corpus striatum, in which the efferent systems and interneurones are affected, along with pronounced gliosis. To a lesser extent, the same phenomenon is observed in the globus pallidus, the thalamus, the substantia nigra, the locus coeruleus and the cortex.

No treatment is currently available to care for or delay the development of Huntington's disease.

It is known that Efaroxan: 2-[2-(2-ethyl-2,3-dihydrobenzofuranyl)]-2-imidazoline, has antagonistic properties on the $\alpha_2$-adrenergic receptors. This compound is described in patent application GB 2,102,422, as is its therapeutic application as an antidepressant and antimigraine medicinal product. This compound is also described in patent application WO 92/05171, which reveals the action of the levo-rotatory enantiomer to treat diabetes, as an agent for blocking the potassium channels.

Our patents WO 94/00715 and WO 94/00841 also relate to the use of Efaroxan in the treatment of Parkinson's disease and in Alzheimer's disease.

The present invention relates to the use of Efaroxan for the preparation of a medicinal product for the treatment of Huntington's disease.

The term Efaroxan refers to the compound of formula:

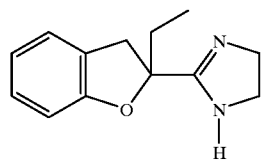

its therapeutically acceptable salts, its racemic mixture or its optically active isomers.

Pharmacological Study

Quinolinic acid, an endogenous metabolic of tryptophan, acts as a powerful agonist on the NMDA receptor (Eur. J. Pharm (1981), 72, 411). When injected into the striatum in rats and monkeys, it causes neurochemical and morphological changes similar to those observed in Huntington's disease (Life Sci. (1984), 35, 19) and are reflected by a deficiency in spatial acuity, cognitive abilities and recall. This attack of the striatum thus accounts for Huntington's disease (Behav. Brain Res. (1987), 24, 125).

In brains affected by the disease, the level of enzyme for the synthesis of quinolinic acid, 3-hydroxy-anthranilate oxygenase (3-HAO), is high. Furthermore, the level of kynurenic acid (another tryptophan metabolite and a quinolinic acid antagonist) is lowered, thus implying a poor balance between these two acids—quinolinic acid and kynurenic acid—in brains affected by Huntington's disease (Pharmacol. Rev. 1993, 45, 309).

Thus, a pharmacological intervention capable of restoring the functions of the striatum in this model can be useful in the treatment of the motor and cognitive manifestations of Huntington's disease in man (J. Neuroscience (1988), 8, 3901 and Pharmacol. Rev. (1993), 45, 309).

The parameters measured are:

1) The activity of choline acetyltransferase (ChAT) in the striatum, which is a marker of the cholinergic neurones in this part of the brain. A reduction in the activity of ChAT, following an intrastriatal injection of quinolinic acid, is a quantitative measure of the loss of striatal cholinergic neurones, and is correlated with the extent of the neurotoxic lesion in that part of the brain. In this model, the ability of a drug to attenuate the loss of ChAT activity, induced by quinolinic acid, is considered as an indication of a protective or restorative effect of the integrity of the striatal cholinergic system. This model used is described by T. W. Stone (Pharmacol. Rev. 1993, 45, 309), M. F. Beal et al. (J. Neurosci. 1988, 8, 3901) and M. Miyamoto and J. T. Coyle (Exptl. Neurol. 1990, 108, 38).

2) The rotational behavior induced by apomorphine, which is an indicator of dysfunction of the efferent striatal system, this model being described by C. J. Pycock (Neuroscience, 1980, 5, 461). That publication reviews the evidence demonstrating that unilateral lesions in the striatum by exitotoxins, such as quinolinic acid, give rise to a rotational (ipsilateral) behavior in animals which have received apomorphine, and that the intensity of these rotations is in relation with the extent of the lesion. The ability of a drug to reduce the number of rotations induced by apomorphine is considered as indicative of a protective or restorative effect of the integrity of efferent striatal neurone function.

The results are as follows:

1) ChAT Activity

ChAT is decreased to 26±8% (mean±SEM) of the normal activity (measured in undamaged striatum), 2 weeks after intrastriatal unilateral injection of quinolinic acid (150 nmol) to rats.

Administration 3 times a day for 7 days of 0.63 mg/kg of Efaroxan from the same day of the injection of quinolinic acid, partially attenuates this loss of ChAT activity. In this case, the activity is reduced only to 56±7% (mean±SEM) of the normal activity, as can be seen in the attached FIG. 1, which illustrates the loss of ChAT activity induced by quinolinic acid in rat striatum, and thus reflects the protective effect exerted.

2) Rotation Behavioral Test

Figure 2:
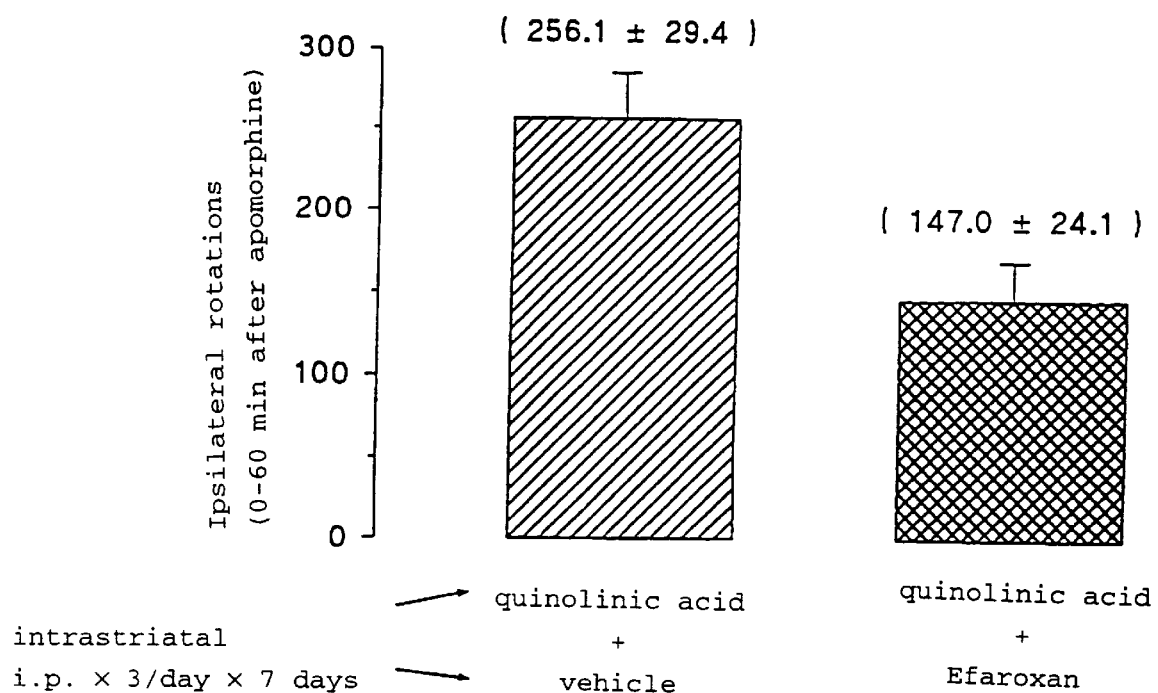

In the animals injured with quinolinic acid as above, an injection of 0.63 mg/kg of apomorphine two weeks later induces an ipsilateral rotation (256±29 rotations/h, mean±SEM). The administration of 0.63 mg/kg of Efaroxan as above, 3 times a day for 7 days, reduces the number of these ipsilateral rotations by 43% (to 147±24 rotations/h, mean±SEM), as shown in the attached FIG. 2 which illustrates the rotations induced by apomorphine in rats injured with quinolic acid and demonstrates the attenuation of the effect by Efaroxan.

The above results show the advantage of Efaroxan for reducing the deleterious excitotoxic effects of quinolinic acid in the striatum, and its advantage in the prevention of neurotoxic disorders in which the glutamate receptors are involved.

Efaroxan thus has an advantage for use as a medicinal product to treat or delay or prevent the development of Huntington's disease.

Pharmaceutical Study

The pharmaceutical compositions forming part of the invention are administered orally to man, in one or more doses, in the form of gelatin capsules or tablets containing a dose of from 1 to 200 mg of active principle, more particularly of 7, 20, 30 and 40 mg per tablet, or intravenously in the form of an injectable solution containing a dose of from 0.1 to 10 mg of Efaroxan.

Clinical Study

Efaroxan was administered at a dose of 30 mg 3 times a day to a group of patients exhibiting the symptomatology of Huntington's disease. The results show an improvement in behavior in about 30% of the cases.

What is claimed is:

1. Method of treating Huntington's Disease comprising the step of administering to a patient suffering therefrom an effective amount of Efaroxan or a therapeutically-acceptable salt thereof in racemic form or in the form of an optically-active isomer thereof.

2. Method of claim 1 wherein the Efaroxan or a therapeutically-acceptable salt thereof is administered orally in the form of a pharmaceutical composition containing 7 to 40 mg of Efaroxan or therapeutically-acceptable salt thereof per unit dosage form.

3. The method of claim 2 wherein the pharmaceutical composition is administered in the form of gelatin capsules or tablets.

4. The method of claim 2 wherein the pharmaceutical composition is administered in unit dosage form a plurality of times a day.

5. The method of claim 4 wherein the pharmaceutical composition is administered in 30 mg dosages three times a day.

6. The method of claim 1 wherein the Efaroxan or therapeutically-acceptable salt thereof is administered in the form of an injectable solution containing 0.1 to 10 mg of Efaroxan or therapeutically-acceptable salt thereof per unit dose.

* * * * *